United States Patent [19]
Mukherjee

[11] Patent Number: 6,022,342
[45] Date of Patent: Feb. 8, 2000

[54] CATHETER INTRODUCER FOR ANTEGRADE AND RETROGRADE MEDICAL PROCEDURES

[76] Inventor: Dipankar Mukherjee, 9911 Rosewood Hill Cir., Vienna, Va. 22182

[21] Appl. No.: 09/088,492

[22] Filed: Jun. 2, 1998

[51] Int. Cl.[7] .................................................. A61M 25/00
[52] U.S. Cl. .......................................... 604/523; 604/528
[58] Field of Search ................................... 604/264, 523, 604/528

[56] References Cited

U.S. PATENT DOCUMENTS

| | | |
|---|---|---|
| D. 272,651 | 2/1984 | Mahurkar . |
| 4,134,402 | 1/1979 | Mahurkar . |
| 4,405,314 | 9/1983 | Cope ......................................... 604/51 |
| 4,543,087 | 9/1985 | Sommercorn et al. . |
| 4,549,879 | 10/1985 | Groshong et al. . |
| 4,552,554 | 11/1985 | Gould et al. .............................. 604/51 |
| 4,671,796 | 6/1987 | Groshong et al. . |
| 4,701,166 | 10/1987 | Groshong et al. . |
| 4,905,667 | 3/1990 | Foerster et al. ............................. 128/4 |
| 4,931,039 | 6/1990 | Coe et al. .................................. 604/53 |
| 4,998,919 | 3/1991 | Schnepp-Pesch et al. ............. 604/164 |
| 5,098,392 | 3/1992 | Fleischhacker et al. . |
| 5,195,978 | 3/1993 | Schiffer ................................... 604/161 |
| 5,295,995 | 3/1994 | Kleiman . |
| 5,337,730 | 8/1994 | Maguire . |
| 5,360,416 | 11/1994 | Ausherman et al. .................... 604/272 |
| 5,364,376 | 11/1994 | Horzewski et al. . |
| 5,413,560 | 5/1995 | Solar . |
| 5,431,648 | 7/1995 | Lev . |
| 5,484,411 | 1/1996 | Inderbitzen et al. . |
| 5,531,700 | 7/1996 | Moore et al. . |
| 5,571,087 | 11/1996 | Ressemann et al. . |
| 5,624,396 | 4/1997 | McNamara et al. . |
| 5,637,091 | 6/1997 | Hakky et al. . |
| 5,658,311 | 8/1997 | Baden . |
| 5,697,905 | 12/1997 | d'Ambrosio . |
| 5,792,118 | 8/1998 | Kurth et al. ............................. 604/246 |
| 5,820,592 | 10/1998 | Hammerslag .............................. 604/95 |

*Primary Examiner*—Corrine McDermott
*Attorney, Agent, or Firm*—Dinesh Agarwal, P.C.

[57] ABSTRACT

A catheter introducer for antegrade and retrograde medical procedures includes a generally tubular introducer member having proximal and distal ends. The introducer member includes a lumen for receiving a guidewire during a medical procedure, which guidewire includes a distal end traveling in a first direction. The catheter introducer further includes an occlusion member adjacent the distal end thereof for altering the traveling direction of the distal end of the guidewire to a second direction. The catheter introducer of the invention can be easily used for performing angioplasty on tandem or segmental lesions in one procedure using antegrade and retrograde approaches. The novel technique of the present invention involves performing angioplasty on one lesion using one of the antegrade and retrograde approaches, and then using the other of the antegrade and retrograde approaches to perform angioplasty on the second lesion. Both lesions are attended to during one medical procedure.

55 Claims, 5 Drawing Sheets

CATHETER INTRODUCER FOR ANTEGRADE AND RETROGRADE MEDICAL PROCEDURES

FIELD AND HISTORICAL BACKGROUND OF THE INVENTION

The present invention is directed to vascular catheters, and more particularly to a catheter introducer which can be used in an antegrade, as well as a retrograde medical procedure.

One of the major causes of morbidity and mortality in modern times is the frequent occurrence of vascular disease. This disease expresses itself in heart attacks, strokes, lower extremity occlusive disease, and aneurysmal disease. The predominant cause of the vascular disease is atherosclerosis, which arises from localized plaque accumulation at various sites in the vascular system, and particularly in the arterial network of a person. Plaque accumulation is caused by deposition of fat, lipid, and the like substances, on the interior walls of blood vessel, which, over time, leads to narrowing of the vascular lumen, a phenomenon medically known as "stenosis". As a result, blood flow is restricted and the person's health may be at serious risk, depending upon various other clinical and health-related factors. In fact, it has been reported that cardiovascular disease is the leading cause of mortality in the developed world and that in the U.S. alone there are approximately 1 million deaths attributable to this disease.

Although atherosclerosis is commonly associated with coronary arteries that feed the heart, other peripheral blood vessels, such as carotid and lower extremity arteries are equally susceptible to plaque formation. As noted above, atherosclerosis is caused by localized plaque build up at certain vulnerable sites in the vascular system, rather than from diffusion. In this regard, the coronary arteries, carotid bifurcation, infrarenal abdominal aorta, and iliofemoral vessels are particularly susceptible, while the thoracic aorta, common and distal internal carotid, mesenteric, renal, intercostal, mammary, and upper extremity arteries tend not to be severely affected.

Numerous techniques for opening constricted blood vessels have been proposed and are currently being used by the medical community. Many devices are also available for use in these techniques. One of the widely used and accepted techniques is known as "balloon angioplasty". This technique involves introducing a catheter through a blood vessel to access the site of plaque formation. The catheter at its tip includes a balloon which is selectively inflated at the site to push or flatten the plaque against the walls of the blood vessels. This results in dilation (or dilatation) of the vessel lumen thereby improving the blood flow. A stent is commonly positioned subsequent to dilatation to prevent plaque regression and for maintaining the integrity of the vessel. Other approaches to dilatation of the blood vessels include, using a cutting or abrasive tool to remove the plaque, using an electric spark to burn through the plaque, and using laser to burn or remove portions of the plaque.

A typical angioplasty procedure is performed by retrograde (upstream of blood flow) introduction of a guidewire from the groin area of a person. An appropriate balloon angioplasty catheter is then advanced over the guidewire to reach the site of plaque formation and then dilatation of the same. This procedure works well where the lesion or plaque formation is present only at one location. However, tandem localized lesions causing lower extremity ischemia may exist in the iliac arterial system, as well as in the superficial femoral artery, and typically at the Hunter's canal. Early in the atherosclerotic disease process, the lesions tend to produce stenosis of the main arterial channel and later in the disease process, segmental arterial lesions or occlusions are encountered.

The balloon angioplasty of iliac arterial stenoses are typically performed by puncturing the common femoral artery on the same side as the lesion and advancing a guidewire across the lesion, followed by placement of an appropriate balloon angioplasty catheter across and dilatation of the same. In the event, the placement of a stent is required across an iliac artery stenosis, a similar approach is taken. In other words, a catheter is introduced from a convenient location that is below the lesion.

As noted previously, segmental occlusions of blood vessels are commonly encountered. For example, one lesion may be found in the iliac arterial system, and another lesion may be found in the superficial femoral artery which is downstream with regards to blood flow. The dilatation of the lesion in the superficial femoral artery requires an antegrade puncture of the ipsilateral common femoral artery, or one may come around the aortic bifurcation from the contralateral femoral artery and then advance a long guidewire across the stenosis in the superficial femoral artery. Neither of these procedures is preferable from a medical or a patient's point of view. From a medical standpoint, both of these approaches require a second cannulation, either an antegrade puncture of the ipsilateral femoral artery or a puncture of the contralateral femoral artery. The second cannulation generally cannot be done immediately after performing angioplasty of the first lesion, for example, in the iliac arterial system, since the first puncture is still fresh and not fully healed. In other words, the second cannulation requires a delay of at least 72 hours, and preferably a delay of at least one week, to allow the first puncture to fully heal. As a result, the patient has to be brought back for the second angioplasty procedure, or requires following a less preferable and difficult approach of the second lesion in the superficial femoral artery from the contralateral femoral artery across the aortic bifurcation.

Both of these procedures can be extremely difficult and cumbersome and are less preferable to patients, as the patient either has to return for a second procedure or encounter two punctures during one procedure, one on each side. The contralateral approach is particularly not preferable from a surgeon's viewpoint, as it requires the use of a long guidewire from one side of a patient to the other and thus leads to maneuverability problems. In addition to being difficult and less preferable to patients and surgeons, these procedures add cost to the overall angioplasty of tandem or segmental lesions in a patient.

Various catheters are currently available for use by the medical community and illustrative examples are shown in U.S. Pat. Nos. 4,549,879 to Groshong et al.; 4,671,796 to Groghong et al.; 4,701,166 to Groshong et al.; 5,098,392 to Fleishhacker et al.; 5,364,376 to Horzewski et al.; 5,531,700 to Moore et al.; 5,571,087 to Ressemann et al.; and, 5,624,396 to McNamara et al. These catheters are not concerned, however, with dilatation of tandem lesions during one medical procedure.

In view of the disadvantages associated with the conventional techniques, there is a need in the industry for a device and technique which allows a surgeon to perform dilatation of tandem or segmental lesions in a patient during one surgical procedure and by making only one puncture of a blood vessel.

OBJECTS AND SUMMARY OF THE INVENTION

The principal object of the present invention is to provide a catheter introducer device which allows a surgeon to perform angioplasty on tandem or segmental occlusions by making only one puncture of a blood vessel on the same side as the occlusions.

Another object of the present invention is to provide a catheter introducer device which allows a surgeon to perform angioplasty on tandem lesions in one procedure.

Yet another object of the present invention is to provide a catheter introducer device which can be used in an antegrade as well as a retrograde medical procedure.

An additional object of the present invention is to provide a catheter introducer device which is inexpensive to manufacture and simple to use in both antegrade and retrograde medical procedures.

Yet an additional object of the present invention is to provide a catheter introducer device which greatly facilitates insertion of a catheter in the areas of a vascular tree that are difficult to approach with angiography.

Still yet an additional object of the present invention is to provide a catheter introducer device which includes a tactile member adjacent proximal end thereof which assists a surgeon in directing the remote distal end portion of the catheter in a desired circular direction within a blood vessel, by providing an immediate feedback as to the orientation of the distal end of the catheter about a rotational plane.

Another object of the present invention is to provide a catheter introducer device which greatly facilitates insertion of a catheter into the vessel branches extending at sharp or acute angles off, for example, the main abdominal or thoracic aorta.

An additional object of the present invention is to provide a medical procedure for dilatation of tandem vascular occlusions in one procedure and without having to bring the patient back at another time.

In summary, the present invention provides a novel catheter introducer device and technique for performing angioplasty procedures on tandem or segmental lesions using antegrade and retrograde approaches. The novel device and technique prevents delay generally associated with conventional techniques, is easy to perform, significantly less cumbersome, efficient, and saves time and effort and financial resources.

BRIEF DESCRIPTION OF THE DRAWINGS

The above and other objects, novel features and advantages of the present invention will become apparent from a review of the detailed description of the invention provided below and as shown in the drawings, in which.

DETAILED DESCRIPTION OF THE PREFERRED EMBODIMENTS OF THE INVENTION

Figure 1:
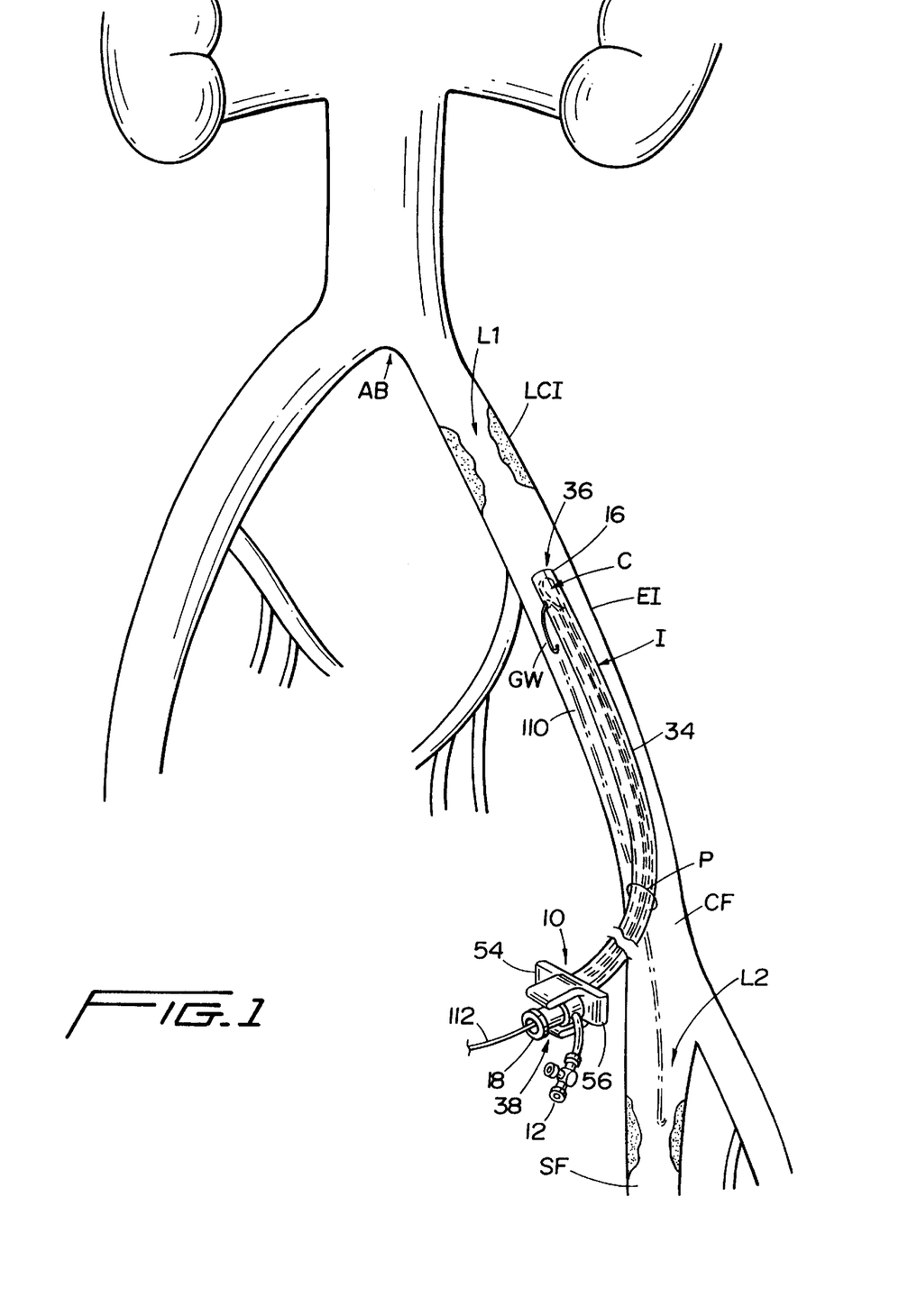
FIG. 1 is a partial schematic illustration of an arterial system, showing the catheter introducer and the peel-away sheath of the present invention within a left external iliac artery approaching a plaque deposit or lesion in the left common iliac artery from a site in the left common femoral artery.

Referring to FIG. 1, the catheter introducer C of the present invention is shown within a peel-away introducer sheath I which includes a gripping clamp mechanism 10 and a valve mechanism 12. The catheter C includes a generally tubular body member 14 with a distal end portion 16 and a proximal end portion 18.

Figures 2, 5:
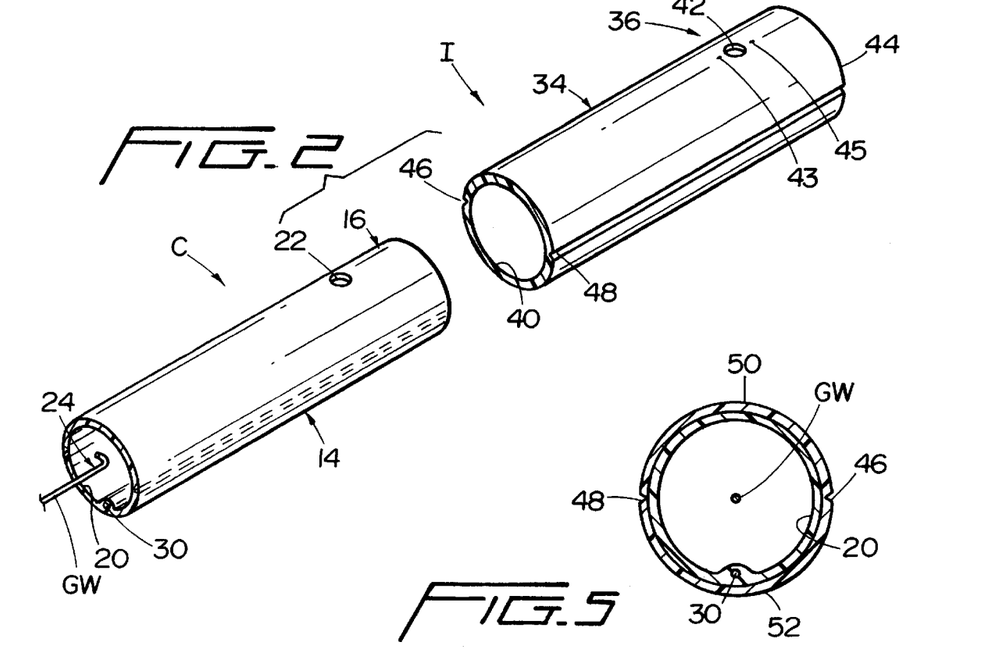
FIG. 2 is an enlarged partial perspective view of the distal end portion of the catheter introducer device of the present invention, shown with a corresponding distal end portion of the optional peel-away sheath of the invention.
FIG. 5 is a sectional view taken along line 5—5 of FIG. 3.
Figure 3:
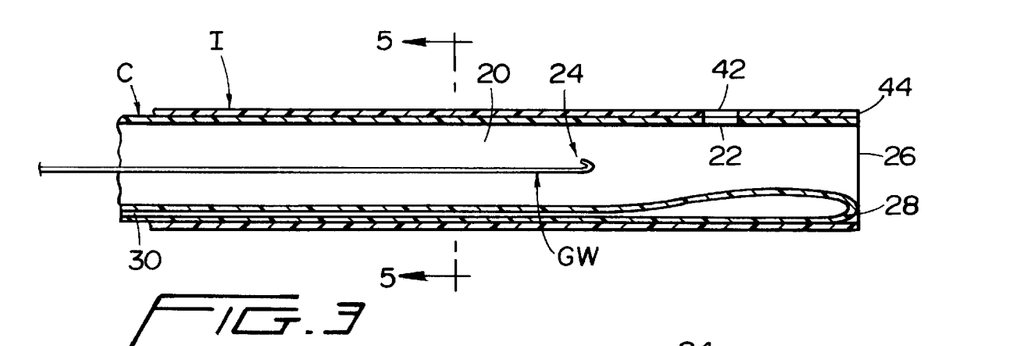
FIG. 3 is a vertical sectional view of the catheter introducer device of FIG. 2, positioned inside the peel-away sheath and showing the inflatable occlusion member in a deflated state.
Figure 4:
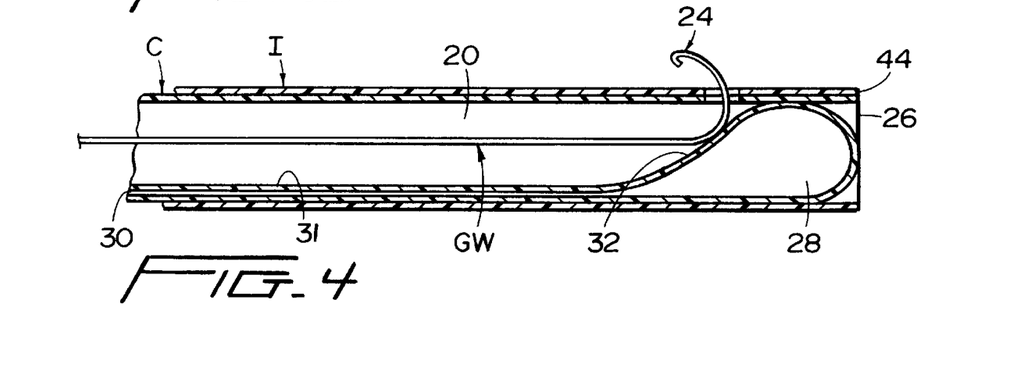
FIG. 4 is a view similar to FIG. 3, showing the occlusion member in the inflated state and supporting the guidewire out of the catheter introducer device of the present invention.

As best shown in FIG. 2, the catheter introducer C includes a lumen 20 for receiving a guidewire. (It is noted, however, that other conventional devices, such as diagnostic catheters, etc, may also be introduced through lumen 20.) A guidewire exit opening 22 is provided in the distal end portion 16 through the wall of the catheter 14. The exit opening 22, as best shown in FIG. 3, communicates with lumen 20 and allows the distal end portion 24 of guidewire GW to extend therethrough. As best shown in FIGS. 3–4, the distal end portion 16 is open at 26 and is provided with an inflatable member 28 in the lumen 20. Upon inflation, the inflatable member 28 assumes the shape of an eccentric, tear-drop shaped balloon and blocks the opening 26.

As best shown in FIG. 2–5, an internal channel 30 communicates with the inflatable member 28 on one end, and is connected with, for example, a source of air (not shown) to inflate the member 28, on the other end. As best shown in FIG. 4, in the inflated state, the member 28 defines an upwardly inclined ramp 32 which guides the distal end portion 24 of guidewire GW towards exit opening 22. In this regard, it is extremely important that the ramp angle relative to the internal surface 31 of the catheter body 14, be selected so as to properly guide the end portion 24 of the guidewire GW through the exit opening 22. Preferably, the angle can be from about 30° to 90°. (It is noted herewith that although a tear-drop shape of the inflatable number 28 is illustrated, it is well within the scope of this invention to provide other shapes and configurations.)

As described below in detail, the catheter introducer C may be used alone, or in combination with the introducer peel-away sheath I of the invention. As best shown in FIGS. 1–2, the sheath I has a tubular body 34 with a distal end portion 36 and a proximal end portion 38. The sheath body 34 also defines a lumen 40, the diameter of which is slightly larger than the external diameter of catheter introducer C. The sheath I is also provided with a peripheral exit opening 42 which communicates with lumen 40, and is open at 44. The exit openings 22 and 42 in catheter introducer C and sheath I, respectively, are provided in the corresponding distal end portions such that they can be in precise alignment with each other when catheter introducer C is inserted through the sheath I (FIGS. 3–4). In this regard, although not shown, proximal end portions 18 and 38 may be provided with indexing members to allow a surgeon to properly position the catheter introducer C within the sheath I such that openings 22 and 42 in the corresponding distal end portions, are easily aligned. Also, as designated by numerals 43 and 45 in FIG. 2, preferably two radio-opaque markers may be provided on the external periphery of sheath body 34 and about the opening 42, to visually indicate the position of the opening 42 on a radioscope to a surgeon.

The peel-away sheath 1, as best shown in FIGS. 2 and 5, is provided with two diametrically opposite weakness lines 46 and 48, to allow it to be separated thereabout into upper and lower sections 50 and 52, by pulling on handles 54 and 56 provided adjacent proximal end portion 38 thereof, in a known manner (FIG. 1). It is noted herewith that the catheter introducer C may also be provided with weakness lines in the like manner, as shown by broken lines in FIG. 2.

Figure 6:
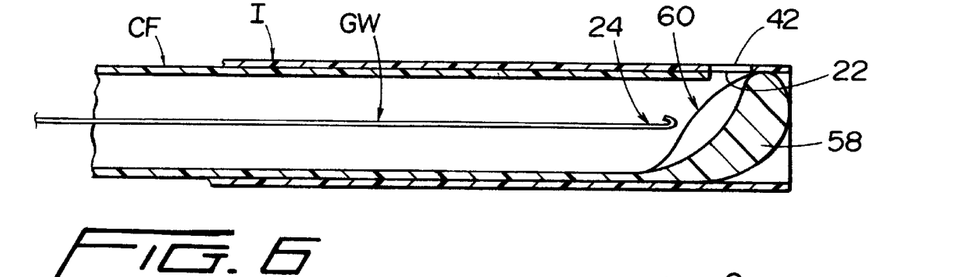
FIG. 6 is a first alternative embodiment of the catheter introducer device shown in FIG. 2.
Figure 7:
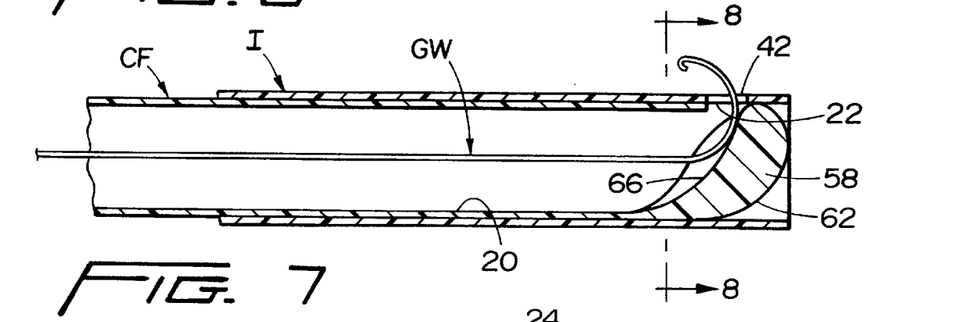
FIG. 7 is a view similar to FIG. 4, showing the first alternative embodiment of the catheter introducer device of the present invention.
Figures 8, 9, 10, 11:
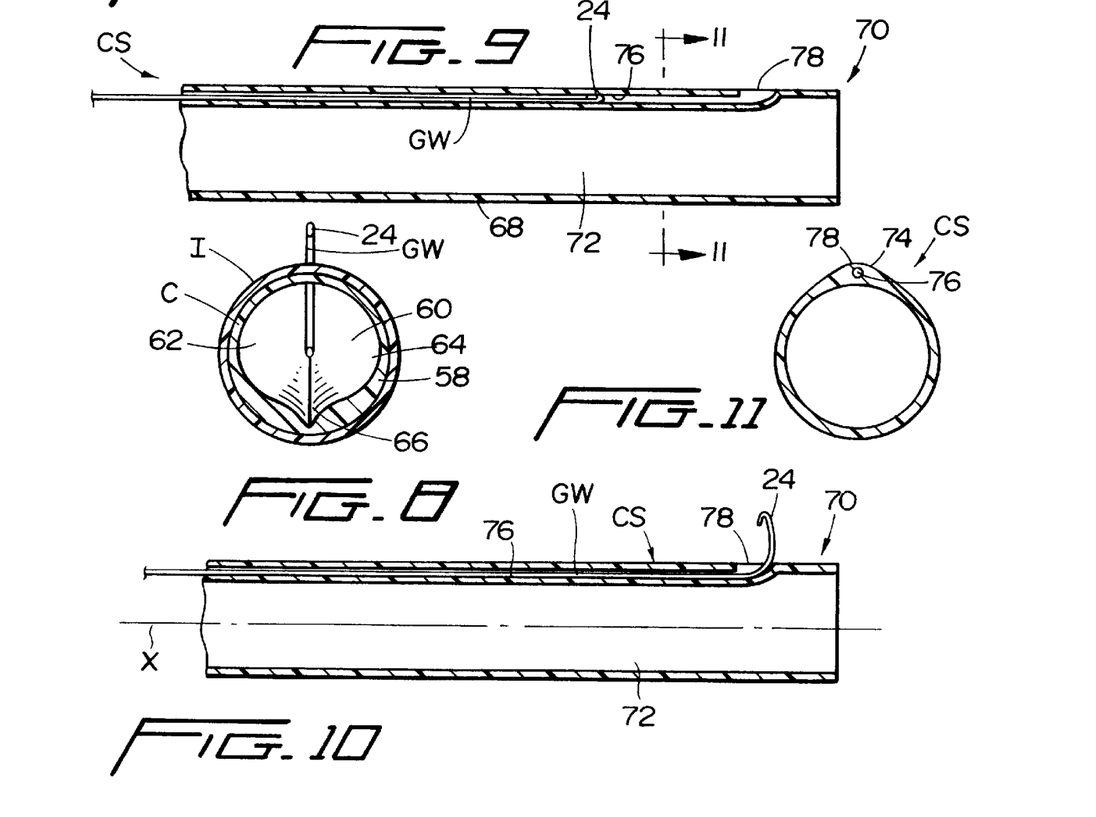
FIG. 8 is sectional view taken along line 8—8 of FIG. 7.
FIG. 9 is a second alternative embodiment of the catheter introducer device shown in FIG. 2.
FIG. 10 illustrates the catheter introducer device of FIG. 9, showing the guidewire extending through the exit hole.
FIG. 11 is a sectional view taken along line 11—11 of FIG. 9.

FIGS. 6 and 7 illustrate a first alternative embodiment of the catheter introducer CF of the invention which is similar to the embodiment shown in FIGS. 1–5, with the exception that the inflatable member is substituted by a somewhat rigid end blocking member 58. As shown, the blocking number 58 is preferably made integral with the catheter introducer C and has a semi-circular configuration defining an upwardly extending ramp 60. As best shown in FIG. 8, ramp 60 includes lateral sections 62 and 64 that together define a central, generally V-shaped groove 66 which guides the distal end portion 24 of the guidewire GW towards the exit openings 22 and 42. (It is noted herewith that in this embodiment and other embodiments described below, the like parts are designated with like numerals as in FIGS. 1–5.)

FIGS. 9–11 illustrate a second alternative embodiment of the catheter introducer of the present invention. In particular, the catheter introducer CS according to the second alternative embodiment, includes a body portion 68 with a distal end portion 70 and a proximal end portion (not shown). The body portion 68 defines therein a main lumen 72. As best shown in FIG. 11, a ridge or projection 74 is formed integrally on the external periphery of the catheter body 68, and a lumen 76 having a diameter substantially corresponding to the diameter of the guidewire GW, extends through the ridge 74 and communicates with a peripheral opening 78 in the distal end portion 70. Preferably, opening 78 extends radially through the thickness of the body portion 68 in the same sectional plane as the lumen 76. In other words, the opening 78 and lumen 76 are vertically aligned, as viewed in FIG. 11.

As illustrated in FIG. 11, the thickness of the catheter body wall is greater in the ridge portion 74 than in the remainder portion thereof. As a result, ridge 74 functions as an external tactile member providing immediate feedback to a surgeon as to the location of the opening 78. In other words, since the lumen 76 (through which the guidewire GW extends) and opening 78 are aligned, a surgeon by feeling the ridge 74, can immediately learn the location of the peripheral opening 78 in a circular direction about the central longitudinal axis X of the catheter introducer CS (FIG. 10). Accordingly, the surgeon by manipulating (or rotating) the proximal end 70 of the catheter introducer CS can accurately predict and properly direct the distal end portion 24 of the guidewire GW through the exit opening 78 in a desired circular direction within or about a blood vessel. This immediate tactile feedback greatly assists a surgeon in knowing in advance in which direction about a circular plane, the distal end portion 24 of the guidewire GW would exit within a blood vessel, and thus assists the surgeon in advancing the guidewire GW toward a desired location.

In this regard, while it is preferable from a practical standpoint that the ridge extend the length of the catheter, it is well within the scope of this invention to provide a ridge or projection only adjacent the proximal end of the catheter that is axially aligned with the guidewire GW exit opening 78. It is further within the scope of this invention to provide an alternative form of the tactile member. For example, a small recess with or without a projection therein, may be provided adjacent the proximal end of the catheter, instead of an outwardly extending ridge or projection illustrated herein.

Figure 12:
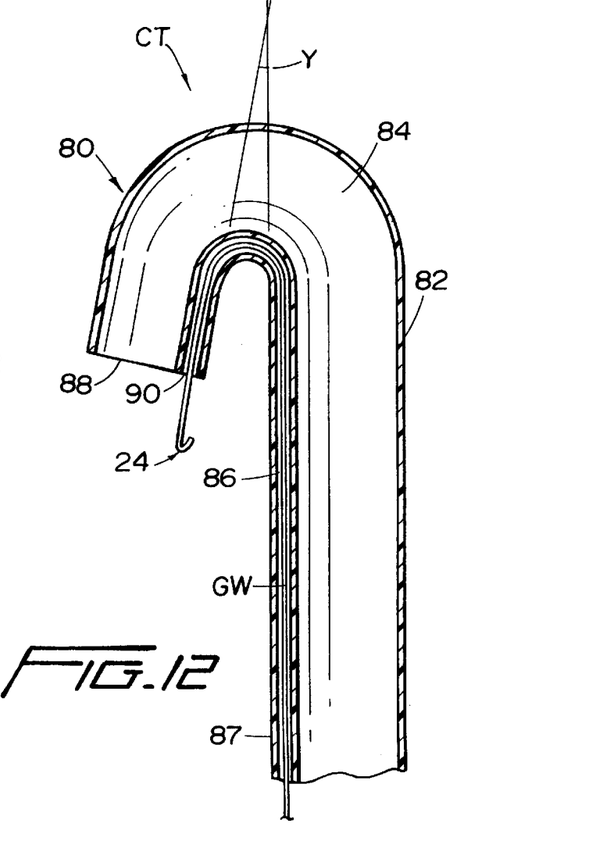
FIG. 12 is a third alternative embodiment of the catheter introducer device shown in FIG. 2.
Figure 13:
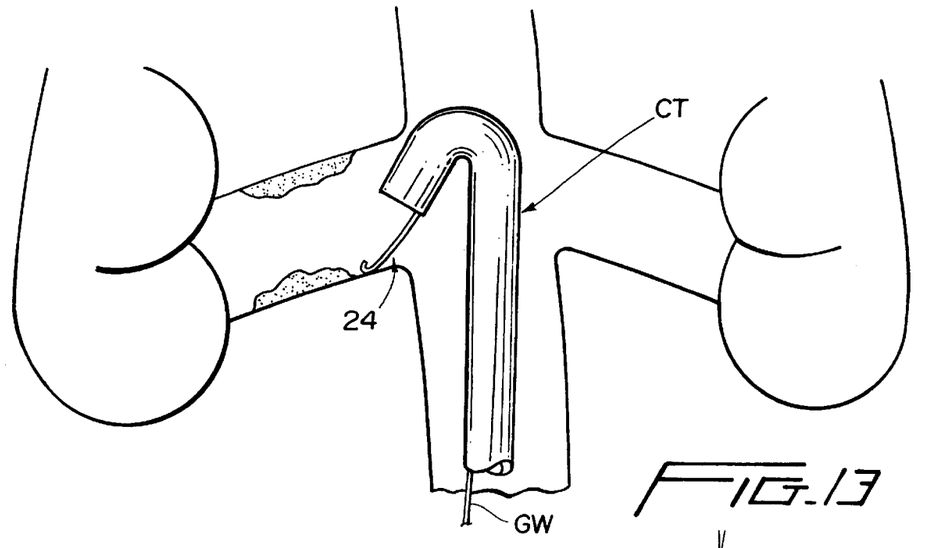
FIG. 13 illustrates the catheter introducer device of FIG. 12 in use for dilatation of a renal artery.

FIGS. 12 and 13 illustrate a third alternative embodiment of the catheter introducer CT of the present invention, which is similar to the embodiment shown in FIGS. 9–11, with the exception that the distal end portion 80 extends at an angle relative to the body portion 82. Moreover, the body portion 82 includes a main lumen 84 and a guidewire GW lumen 86, which extend generally parallel to one another and communicate with end openings 88 and 90, respectively. Preferably, the distal end portion forms an angle Y of about 0° to 180°. As best shown in FIG. 13, the catheter introducer CT of this embodiment greatly facilitates the surgeon to properly and precisely direct the distal end portion 24 of the guidewire GW, to places within the vascular tree that extend at various angles, and particularly acute angles, relative to the main aorta. In addition, the tactile member 87 further allows a surgeon to extend the guidewire GW in a desired circular direction within or about a blood vessel.

Figure 14:
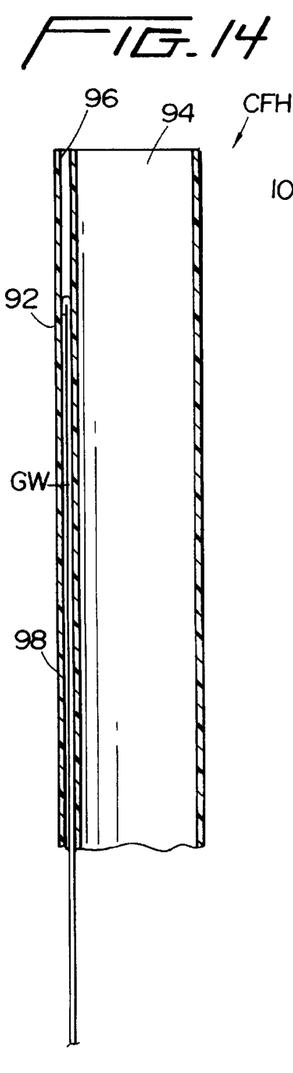
FIG. 14 is a fourth alternative embodiment of the catheter introducer device shown in FIG. 2.

FIG. 14 illustrates a fourth alternative embodiment of the catheter introducer CFH of the present invention, which is similar to the embodiment shown in FIGS. 12–13, with the exception that the entire body portion 92 is rectilinear in configuration. As in the embodiments shown in FIGS. 9–13, the catheter introducer CFH of this embodiment also includes a main lumen 94, and a guidewire lumen 96 which extends within an external ridge or projection 98 to provide tactile feedback to a user.

Figure 15:
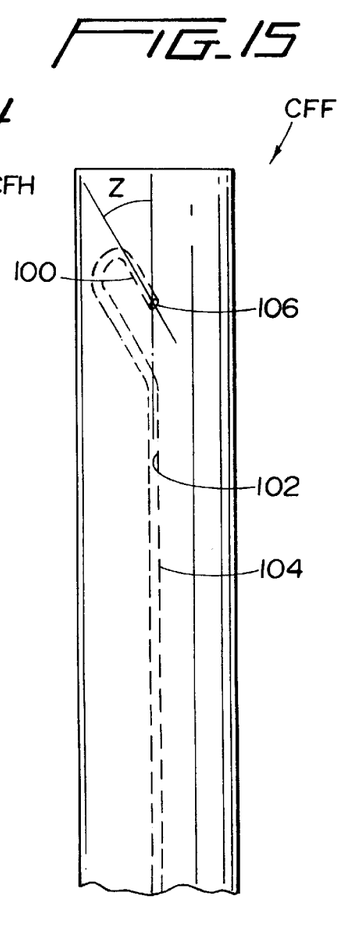
FIG. 15 is a fifth alternative embodiment of the catheter introducer device of FIG. 2, shown without a guidewire.
Figure 16:
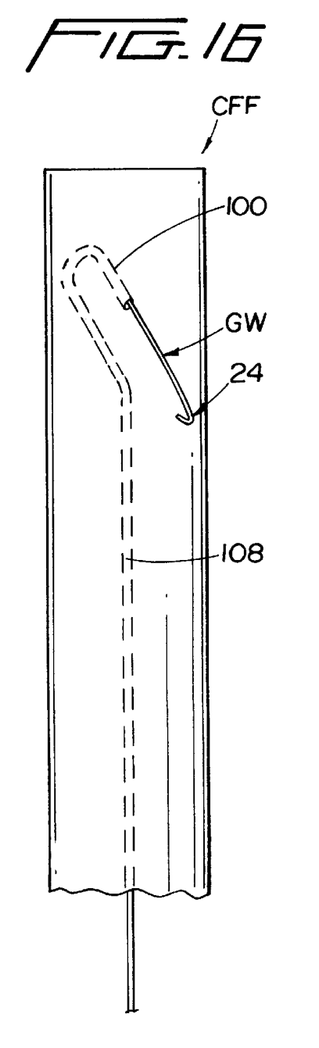
FIG. 16 illustrates the catheter introducer device of FIG. 15, showing the guidewire in place.

FIGS. 15 and 16 illustrate a fifth alternative embodiment of the catheter introducer CFF of the present invention, which is similar to the embodiments shown in FIGS. 9–11, with the exception that the distal end portion 100 of the guidewire lumen 102 extends at an angle relative to the main body 104 of lumen 102. In particular, distal end portion 100 of the lumen 102 extends at an angle Z of about 0° to 180°. It should be noted herewith that although the distal end portion 100 extends at an angle relative to the main lumen body 104, the guidewire exit opening 106 is in axial alignment with the lumen body 104. Since as in the embodiment shown in FIGS. 9–11, the guidewire GW lumen 102 extends through a projection or ridge 108, a surgeon by tactically observing the location of the projection in a circular direction on the periphery of the catheter body, can easily and precisely direct the distal end portion 24 of the guidewire GW out through the opening 106 in a desired direction about the circular plane within a blood vessel.

USE AND OPERATION

As noted above, a typical angioplasty procedure involves introducing a short guidewire through, for example, a Seldinger needle into a selected artery. An introducer sheath is then advanced over the guidewire and positioned to protect the insertion site. The short guidewire is then substituted by a torquable, soft-tipped guidewire which is advanced with the assistance of fluoroscopy to the site of stentosis or occlusion and then continued a reasonable distance beyond the lesion. Once the guidewire is in the correct position, a diagnostic catheter is advanced to the lesion to record various arterial pressures above and below the lesion. Once the diagnosis of the site has been completed, the diagnostic catheter is removed and a balloon catheter is advanced over the guidewire for performing angioplasty on the lesion. Upon completion of the procedure, the guidewire is withdrawn and a new arterial hemodynamic profile is taken. The introducer sheath may then be removed immediately or after a period of time and local compression is applied to obtain hemostasis. The patient is then allowed to rest for a period of time as recommended by the surgeon.

The above is a general procedure that can be followed to perform angioplasty on one lesion. However, if tandem or segmental lesions are present, another procedure would be immediately followed by using the device and technique of the present invention described below.

The technique of the present invention is hereinafter illustrated in terms of tandem lesions L1 and L2, one in the left common iliac artery LCI, and the other in the superficial femoral artery SF (FIG. 1). The dilatation of the iliac lesion L1 is done by cannulating the ipsilateral common femoral artery CF by using the conventional retrograde technique as provided above, wherein a guidewire is advanced upstream of blood flow into the external iliac artery EI to reach the lesion L1. A conventional dilator and the peel-away sheath I of the invention are then introduced over the guidewire to the lesion. Upon completion of the angioplasty procedure on the lesion L1, the guidewire and dilator are removed leaving the peel-away sheath I in place, and one of the catheter introducers of the present invention, preferably C, CF, or CS, is then introduced into the peel-away sheath I.

Figure 17:
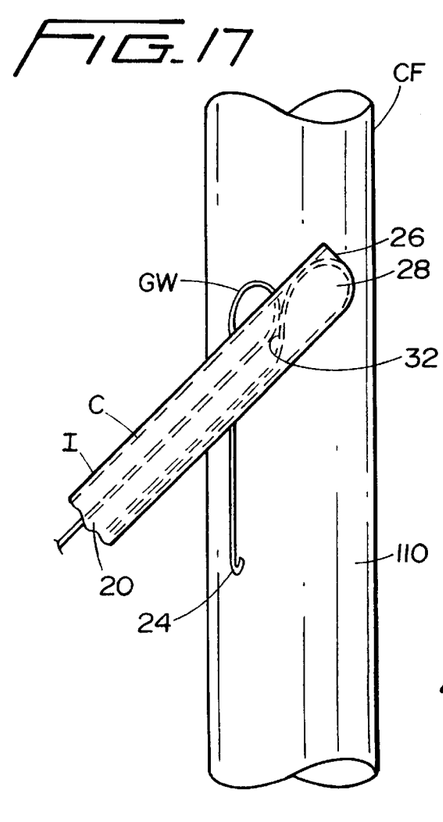
FIG. 17 is a partial enlarged view of the catheter introducer shown in FIG. 1.

The guidewire GW, which has a distal J-shaped end, is then advanced through the lumen 20. At an appropriate time, the member 28 would be inflated to block opening 26 in the catheter introducer I. When the guidewire GW is further advanced through the lumen 20, the ramp 32 would guide the distal end 24 of the guidewire GW out through the aligned exit openings 22 and 42 and into the arterial lumen 110 to follow an antegrade approach (FIG. 17). Upon continuous manipulation of the proximal end 112 of the guidewire GW, the distal end 24 thereof can be advanced toward the lesion L2 in the superficial femoral artery SF. With the guidewire GW in position in the superficial femoral artery SF, the introducer sheath I is then removed by peeling away about weakness lines 46 and 48. The guidewire GW is then advanced across the lesion L2 and when properly in position across the lesion, an appropriate angioplasty catheter is advanced over the guidewire GW to reach the site.

The balloon angioplasty of the lesion L2 is then performed using the standard technique.

One can readily observe from the above that the novel catheter introducer and peel-away sheath of the invention allow a surgeon to perform angioplasty on the lesion L1 by making a retrograde approach through a puncture P in the ipsilateral common femoral artery CF, and then perform the angioplasty on the second lesion L2 by making an antegrade approach through the same puncture P. The angioplasty on both lesions L1 and L2 is therefore performed in one procedure, as opposed to performing angioplasty on one lesion first and then bringing the patient back on another day to perform the angioplasty on the second lesion, or having to approach the second lesion from the contralateral femoral artery and across the aortic bifurcation AB to reach the second lesion in the superficial femoral artery SF.

In this regard, it is noted herewith that although the novel technique of performing angioplasty on two lesions has been illustrated by using both the catheter introducer C and the peel-away sheath I, angioplasty on tandem lesions can be easily performed by using only the catheter introducer of the present invention. In particular, after completing one angioplasty on one lesion, the catheter introducer of the present invention can be advanced over a conventional guidewire which would be left in place within the vascular lumen. The guidewire may then be retracted completely, and guidewire GW inserted so as to allow its distal end portion to exit through the opening 22 to approach the second lesion.

Although the catheter introducers shown in FIGS. 9–16, may be used to perform angiplasty on lesions at any vascular site, they are particularly useful in approaching the lesions in blood vessels which extend at various angles relative to the main vessel. In particular, these catheter introducers are provided with an external ridge or projection which functions as a tactile member providing immediate feedback to a surgeon as to the location of the exit opening for the guidewire GW on the catheter. By knowing in advance, in which direction about a circular plane within a blood vessel, the guidewire GW would exit, the surgeon can easily and properly make the precise approach towards a side branch of a main vessel.

From the above, one can readily appreciate that the novel catheter introducers and the technique of the present invention provide a very effective and easy way to perform angioplasty on vascular lesions, and particularly on tandem or segmental lesions at various sites in the vascular tree of a patient. Further, novel introducers and the technique would greatly assist a surgeon in confidently approaching lesion sites that are tough to reach by using conventional devices which are extremely difficult to manipulate and maneuver. Finally, the introducers and technique of the invention would be preferable to both the patients and the surgeons over conventional techniques, as angioplasty can be performed on tandem or segmental lesions during one procedure by making only one puncture of a selected blood vessel, thereby leading to a comfortable and faster recovery, and in a cost-effective manner.

While this invention has been described as having preferred embodiments, it is understood that it is capable of further modifications, uses and/or adaptations following in general the principle of the invention, and including such departures from the present disclosure as those come within the known or customary practice in the art to which the invention pertains, and as may be applied to the central features hereinsetforth and fall within the scope of the invention and the limits of the appended claims.

What I claim is:

1. A catheter introducer for an antegrade or a retrograde medical procedure, comprising:
   a) a generally tubular introducer member including first and second ends;
   b) said introducer member including a lumen for receiving a guidewire during a medical procedure, the guidewire including a distal end for traveling in a first direction; and
   c) means operably associated with said introducer member for altering the direction of travel of the distal end of the guidewire to a second direction substantially opposite to said first direction.

2. The catheter introducer of claim 1, wherein:
   a) said first and second ends of said introducer member comprise proximal and distal ends, respectively; and
   b) said means for altering the direction of travel comprises an occlusion means provided adjacent the distal end of said introducer member.

3. The catheter introducer of claim 2, wherein:
   a) said introducer member includes an opening adjacent the distal end thereof for allowing the distal end of the guidewire to exit therethrough.

4. The catheter introducer of claim 3, wherein:
   a) said occlusion means comprises an inflatable member positioned adjacent said opening.

5. The catheter introducer of claim 4, wherein:
   a) said inflatable member includes a deflated state and an inflated state; and
   b) said inflatable member in said inflated state defines a ramp for guiding the distal end of the guidewire toward said opening.

6. The catheter introducer of claim 5, wherein:
   a) said inflatable member in said inflated state comprises a generally eccentric balloon.

7. The catheter introducer of claim 3, wherein:
   a) said occlusion means comprises a blocking member positioned adjacent said opening.

8. The catheter introducer of claim 7, wherein:
   a) said blocking member includes a ramp; and
   b) said ramp defines a channel for guiding the distal end of the guidewire toward said opening.

9. The catheter introducer of claim 7, wherein:
   a) said blocking member comprises a generally semicircular member made of a rigid material.

10. The catheter introducer of claim 3, wherein:
    a) said introducer member includes first and second generally opposed weakness lines extending along the length thereof for allowing splitting of said introducer member.

11. The catheter introducer of claim 1, in combination with a guidewire.

12. The catheter introducer of claim 1, in combination with a peel-away sheath for operably associating with said introducer member.

13. A catheter introducer for an antegrade or a retrograde medical procedure, comprising:
    a) a generally tubular introducer member comprising a periphery and including proximal and distal ends and having a central longitudinal axis;
    b) said tubular member including a lumen for receiving a guidewire during a medical procedure, the guidewire including a distal end for traveling in a first direction;
    c) a peripheral opening in said tubular member adjacent the distal end thereof for allowing the distal end of the guidewire to exit therethrough;
    d) means operably associated with said introducer member for altering the direction of travel of the distal end of the guidewire to a second direction; and
    e) said periphery including tactile means for allowing orientation of said peripheral opening in a desired circular direction about the central longitudinal axis of said introducer member.

14. A catheter introducer of claim 13, wherein:
    a) said introducer member includes internal and external peripheries;
    b) said tactile means comprises a projection; and
    c) said external periphery includes said projection.

15. The catheter introducer of claim 14, wherein:
    a) said projection is in general axial alignment with said opening.

16. The catheter introducer of claims 14, wherein:
    a) said projection comprises an elongated ridge generally axially aligned with said opening.

17. The catheter introducer of claim 13, wherein:
    a) said tactile means comprises an external ridge extending the length of said introducer member; and
    b) said lumen extends within said ridge.

18. The catheter introducer of claim 17, wherein:
    a) said means for altering the direction of travel includes a ramp disposed in said lumen; and
    b) said ramp is in general alignment with said opening.

19. A catheter introducer, comprising:
    a) a generally tubular introducer member including proximal and distal ends and having a central longitudinal axis;
    b) said introducer member including first and second lumens and an opening about the periphery thereof;
    c) one of said first and second lumens for receiving a guidewire during a medical procedure;
    d) said one of said first and second lumens communicating with said opening; and
    e) tactile means operably associated with said introducer member and disposed in a common plane with said opening for allowing orientation of said opening in a desired circular direction about the central axis of said introducer member.

20. The catheter introducer of claim 19, wherein:
    a) the distal end of said tubular member includes first and second sections; and
    b) said first section extends at an angle relative to said second section.

21. The catheter introducer of claim 20, wherein:
    a) said angle comprises about 0° to about 180°.

22. The catheter introducer of claim 19, wherein:
    a) said one of said first and second lumens includes a diameter smaller than the diameter of the other of said first and second lumens.

23. The catheter introducer of claim 19, wherein:
    a) said tactile means comprises a projection disposed about the external periphery of said introducer member.

24. The catheter introducer of claim 23, wherein:
    a) said projection comprises an elongated ridge extending the length of said introducer member.

25. The catheter introducer of claim 24, wherein:
    a) said one of said first and second lumens is positioned within said ridge.

26. A catheter introducer, comprising:
    a) a generally tubular introducer member comprising a periphery and including proximal and distal ends and having a central longitudinal axis;

b) said introducer member including a lumen for receiving a guidewire during a medical procedure;
c) said introducer member including an opening about the periphery thereof,
d) said lumen communicating with said opening for allowing the guidewire to exit therethrough; and
e) the periphery including tactile means aligned with said opening for allowing orientation of said opening in a desired circular direction about the central axis of said introducer member.

27. The catheter introducer of claim 26, wherein:
a) said tactile means comprises a projection.

28. The catheter introducer of claim 26, wherein:
a) said tactile means comprises an elongated ridge generally axially aligned with said opening.

29. The catheter introducer of claim 28, wherein:
a) said lumen extends through said ridge.

30. The catheter introducer of claim 26, wherein:
a) said lumen includes proximal an d distal ends and a body portion extending therebetween; and
b) the distal end of said lumen includes an end section extending at an angle relative to the body portion of said lumen.

31. The catheter introducer of claim 30, wherein:
a) said angle is about 0° to about 180°.

32. A catheter introducer, comprising:
a) a generally tubular introducer member comprising a periphery and including first and second ends and having a central longitudinal axis;
b) said introducer member including a lumen for receiving a guide member during a medical procedure;
c) said introducer member including an opening about the periphery thereof and communicating with said lumen for allowing the guidewire to exit therethrough;
d) the periphery including a tactile member in general operable alignment with said opening; and
e) said tactile member allowing orientation of said opening in a desired circular direction about the central axis of said introducer member.

33. The catheter introducer of claim 32, wherein:
a) said first and second ends comprise proximal and distal ends, respectively;
b) said tactile member comprises an external projection located adjacent the proximal end of said introducer member; and
c) said opening is located adjacent the distal end of said introducer member.

34. The catheter introducer of claim 33, wherein:
a) said projection extends between the proximal and distal ends of said introducer member.

35. The catheter introducer of claim 33, wherein:
a) said projection comprises an external ridge extending between the proximal and distal ends of said introducer member.

36. The catheter introducer of claim 35, wherein:
a) said lumen extends through said projection.

37. A catheter introducer for an antegrade or a retrograde medical procedure, comprising:
a) a generally tubular introducer member including first and second ends;
b) said introducer member including only a single lumen for receiving a guidewire during a medical procedure, the guidewire including a distal end for traveling in a first direction;
c) means for altering the direction of travel of the distal end of the guidewire to a second direction;
d) said first and second ends of said introducer member comprising proximal and distal ends, respectively;
e) said means for altering the direction of travel comprising an occlusion means provided adjacent the distal end of said introducer member;
f) said introducer member including an opening adjacent the distal end thereof for allowing the distal end of the guidewire to exit therethrough;
g) said occlusion means comprising a blocking member positioned adjacent said opening; and
h) said blocking member completely occluding said lumen.

38. A catheter introducer for an antegrade or a retrograde medical procedure, comprising:
a) a generally tubular introducer member including proximal and distal ends;
b) said introducer member including a lumen for receiving a guidewire during a medical procedure, the guidewire including a distal end for traveling in a first direction;
c) means operably associated with said introducer member for altering the direction of travel of the distal end of the guidewire to a second direction;
d) said means for altering the direction of travel comprising an occlusion means provided adjacent the distal end of said introducer member;
e) said introducer member including an opening adjacent the distal end thereof for allowing the distal end of the guidewire to exit therethrough; and
f) said occlusion means comprising an inflatable member positioned adjacent said opening.

39. The catheter introducer of claim 38, wherein:
a) said inflatable member includes a deflated state and an inflated state; and
b) said inflatable member in said inflated state defines a ramp for guiding the distal end of the guidewire toward said opening.

40. The catheter introducer of claim 39, wherein:
a) said inflatable member in said inflated state comprises a generally eccentric balloon.

41. The catheter introducer of claim 39, wherein:
a) said ramp is inclined at an angle of about 30° to about 90° relative to the internal surface of said introducer member.

42.. A catheter introducer for an antegrade or a retrograde medical procedure, comprising:
a) a generally tubular introducer member including proximal and distal ends and having a central longitudinal axis;
b) said tubular member including a lumen for receiving a guidewire during a medical procedure, the guidewire including a distal end for traveling in a first direction;
c) a peripheral opening in said tubular member adjacent the distal end thereof for allowing the distal end of the guidewire to exit therethrough;
d) means operably associated with said introducer member for altering the direction of travel of the distal end of the guidewire to a second direction;
e) tactile means operably associated with said introducer member for allowing orientation of said peripheral opening in a desired circular direction about the central longitudinal axis of said introducer member;

f) said tactile means comprising an external ridge extending the length of said introducer member; and g) said lumen extending within said ridge.

43. The catheter introducer of claim 42, wherein:

a) said means for altering the direction of travel includes a ramp disposed in said lumen; and b) said ramp is in general alignment with said opening.

44. A catheter introducer, comprising:

a) a generally tubular introducer member including proximal and distal ends and having a central longitudinal axis;

b) said introducer member including a lumen for receiving a guidewire during a medical procedure;

c) said introducer member including an opening about the periphery thereof;

d) said lumen communicating with said opening for allowing the guidewire to exit therethrough;

e) tactile means operably associated with said introducer member and aligned with said opening for allowing orientation of said opening in a desired circular direction about the central axis of said introducer member;

f) said tactile means comprising an elongated ridge generally axially aligned with said opening; and g) said lumen extending through said ridge.

45. A kit for use in an antegrade or a retrograde medical procedure, comprising:

a) a generally tubular introducer member including a lumen;

b) a sheath for operably associating with said introducer member;

c) a guidewire including a distal end for traveling through the lumen of said introducer member in a first direction; and d) said introducer member including means for altering the direction of travel of the distal end of the guidewire to a second direction substantially opposite to said first direction.

46. The kit of claim 45, wherein:

a) said sheath comprises a peel-away sheath.

47. The kit of claim 45, wherein:

a) said introducer member includes first and second generally opposed weakness lines for allowing splitting of said introducer member.

48. The kit of claim 45, wherein:

a) said introducer member includes proximal and distal ends and a central longitudinal axis; and b) said introducer member includes a peripheral opening adjacent the distal end thereof to allow the distal end of the guidewire to exit therethrough.

49. The kit of claim 48, wherein:

a) said sheath includes proximal and distal ends; and b) said sheath includes a peripheral opening corresponding to the peripheral opening in said introducer member.

50. The kit of claim 48, wherein:

a) said introducer member includes tactile means located about the periphery thereof for allowing orientation of said peripheral opening about the central longitudinal axis of said introducer member.

51. The kit of claim 50, wherein:

a) said tactile means comprises a projection.

52. A medical procedure for dilatation of first and second spaced vascular occlusions, comprising the steps of:

a) selecting a site for cannulation on a person's body;

b) performing dilatation of one of said first and second occlusions using one of antegrade and retrograde approaches and through said site; and c) performing dilatation of the other of said first and second occlusions using the other of said antegrade and retrograde approaches and through the same said site.

53. The medical procedure of claim 52, wherein:

said steps b) and c) are performed during one surgical procedure.

54. The medical procedure of claim 52, wherein:

said step c) is performed by using a catheter introducer, comprising:

a generally tubular introducer member including first and second ends;

said introducer member including a lumen for receiving a guidewire including a distal end traveling in a first direction; and means for altering the direction of travel of the distal end of the guidewire to a second direction.

55. The medical procedure of claim 54, wherein:

said first and second ends of said introducer member comprise proximal and distal ends, respectively; and said guidewire direction of travel altering means comprises an occlusion provided adjacent the distal end of said introducer member.

* * * * *